US008259535B2

(12) United States Patent
Sandu et al.

(10) Patent No.: US 8,259,535 B2
(45) Date of Patent: Sep. 4, 2012

(54) WAKE UP STIMULUS CONTROL SYSTEM

(75) Inventors: Daniel Eduardt Sandu, Graz (AT);
Harko Jan Taekema, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 490 days.

(21) Appl. No.: 12/523,166

(22) PCT Filed: Jan. 17, 2008

(86) PCT No.: PCT/IB2008/050168
§ 371 (c)(1),
(2), (4) Date: Jul. 15, 2009

(87) PCT Pub. No.: WO2008/090494
PCT Pub. Date: Jul. 31, 2008

(65) Prior Publication Data
US 2010/0278016 A1 Nov. 4, 2010

(30) Foreign Application Priority Data
Jan. 22, 2007 (EP) .................... 07100872

(51) Int. Cl.
G04B 47/00 (2006.01)
G04B 47/06 (2006.01)
G04C 21/16 (2006.01)
F21V 33/00 (2006.01)

(52) U.S. Cl. .............. 368/10; 368/11; 368/73; 368/256; 362/253

(58) Field of Classification Search ...... 368/10, 368/72, 73, 79, 245, 250, 256, 11, 12; 362/153, 362/253
See application file for complete search history.

(56) References Cited

U.S. PATENT DOCUMENTS

| 3,727,395 A | * | 4/1973 | Baylor ............ 368/256 |
| 3,798,889 A | * | 3/1974 | Chadwick ......... 368/73 |
| 5,008,865 A | * | 4/1991 | Shaffer et al. ..... 368/10 |
| 5,212,672 A | * | 5/1993 | Loisch et al. ..... 368/79 |
| 5,243,568 A | | 9/1993 | Burch et al. |
| 5,402,396 A | * | 3/1995 | Jones, Jr. ......... 368/250 |
| 6,229,430 B1 | | 5/2001 | Dewey |
| 6,236,622 B1 | | 5/2001 | Blackman |
| 6,902,296 B2 | | 6/2005 | Searfoss |
| 2003/0080872 A1 | | 5/2003 | Gutta et al. |
| 2003/0095476 A1 | | 5/2003 | Mollicone et al. |
| 2003/0222587 A1 | | 12/2003 | Dowling et al. |
| 2004/0066710 A1 | | 4/2004 | Yuen et al. |

FOREIGN PATENT DOCUMENTS
GB 2397942 A 8/2004
KR 1020040032344 A 4/2004
* cited by examiner Primary Examiner — Vit W Miska

(57) ABSTRACT

The invention relates to a wake up stimulus control system, comprising a control unit (1) arranged to receive a user-determinable wake up time input and to control at least one stimulus source (11), a coupling for operably coupling at least one stimulus source (11) to said control unit, wherein the stimulus source (11) is controllable by the control unit (1) in such a way that the stimulus source (11) provides a gradually increasing stimulus output in dependence on said input wake up time, at least during a time period before the input wake up time, and at least one stimulus sensor (7) that is operably coupled to the control unit (1). The sensor allows a much better control of the supplied stimulus level to account for various ambient influences. The stimulus is preferably light. The invention also provides a socket, a stimulus source and a control unit for use in the system.

16 Claims, 2 Drawing Sheets

WAKE UP STIMULUS CONTROL SYSTEM

FIELD OF THE INVENTION

The invention relates to wake up stimulus control system, and also to a stimulus source and lamp socket for such a system, and to a stimulus control device.

In particular, the invention relates to a wake up stimulus control system, comprising a control unit arranged to receive a user-determinable wake up parameter input and to control at least one stimulus source that is arranged to supply a wake up stimulus, and a coupling for operably coupling said at least one stimulus source to said control unit, wherein the at least one stimulus source is controllable by the control unit in such a way that the stimulus source provides a gradually increasing stimulus output, in dependence on said input wake up parameter.

BACKGROUND OF THE INVENTION

Document US 2003/0095476 describes an apparatus for a waking control system. The apparatus comprises a detection system for measuring a parameter correlated to an individual's sleep level, and a system controller for introducing a stimulus based on this parameter, before a user-settable wake up time. The apparatus is intended to gradually introduce the stimulus, such as light, before the planned wake up time, in order to wake the individual gradually to promote wellness. It is further described to take into account the seasonal amount of light, as determined by the date.

A disadvantage of the known apparatus is that, in practice, it does not always function properly. Sometimes it happens that the user is woken too early, and at other times he is woken too late, or even not at all, at least not by the apparatus.

SUMMARY OF THE INVENTION

It is an object of the invention to provide a more reliable wake up stimulus control system of the kind mentioned above.

This object is achieved with the system of claim 1, that is characterized in that the system further comprises at least one stimulus sensor arranged for sensing said wake up stimulus, which stimulus sensor is operably coupled to the control unit. It was found that the actually perceived stimulus level influences the reliability of the system. The actually perceived stimulus level may vary according to numerous causes. In order to take into account such variations, a stimulus sensor is included that is able to determine an actual stimulus level. The control unit may then take into account the measured stimulus level. In this way, one becomes able to account for or correct influences such as changing stimulus sources, or positions thereof and so on. This greatly improves the reliability of the waking up of the sleeper.

A number of examples and embodiments will be given below, as well as in the dependent clams, to elucidate further some advantages of including a stimulus sensor.

An important remark to be made here is that, although the invention is called a wake up stimulus control system, the same considerations also hold for bringing an individual gradually to sleep, e.g. simply by gradually decreasing the stimulus level. For simplicity, when the words "wake up" or their equivalents are used, "bringing to sleep" and its according equivalents are intended to be included.

In the present context, "a coupling for operably coupling" means a coupling wherein there is some link, connection or the like, such that the stimulus source is controllable by the control unit. There need not be a physical coupling, and there may e.g. be a wireless network or the like.

Furthermore, "gradually increasing" here means: increasing in more than a few steps from a substantially zero to a stimulus output above a certain threshold, such that sudden jumps that suddenly awake a person are avoided. Of course, a continuous increase is also included, as well as the corresponding decrease in the case of putting a person to sleep. The stimulus output ratios or the absolute differences of the stimulus outputs of the consecutive steps should be comparable to each other. Flash- or burst-like increases, such as from zero output to 10% of maximum output or more are preferably avoided. Hence, for example when using light, the normal fluorescent lamp start-up while tube temperature increases to its optimum temperature, is not included. Since the whole waking up process relates to sleeping people, e.g. with closed eyes, a possibility could be to have steps, such that the human eye cannot discern the steps, e.g. with closed eye lids. The skilled person may come up with analogous definitions of gradually. Importantly, it is not necessary for the stimulus source, or system as a whole, to reach a maximum output level in any of the cases indicated above. A maximum could be reached after a further increase.

Controlling the stimulus source in dependence on said input wake up parameter may mean, for the control unit, to provide a simple start-up signal, for example if some external stimulus source takes care of further regulating the stimulus output. Preferably, the control unit is arranged such that it can control by itself a stimulus output of the stimulus source. For example, it comprises a controllable power supply. Other arrangements are possible, some of which will be elaborated.

Note that, if a claim or embodiment, relates to "at least one item", and an example or the like is described with respect to a single such item, the plural is deemed also included.

In particular, said wake up parameter comprises a desired wake up time, and the at least one stimulus source provides said gradually increasing stimulus output at least during a time period before the input desired wake up time. In many cases, this is a useful wake up parameter, since often it is important to set such time, for example in view of appointments such as working hours. However, it is also possible to use other parameters, such as a desired putting-to-sleep period, that may be set in dependence on how tired the user is, or a desired starting time for waking up or starting to put to sleep.

In embodiments, the stimulus comprises light. In other words, the wake up stimulus control system then is, or comprises, a wake up lighting control system, the stimulus source comprises a light source, and the stimulus sensor comprises a light sensor. Light is an important stimulus in the process of controlled waking up. It is furthermore easily controlled and may be supplied very locally. In the context of the present invention, a preferred type of stimulus is light, although other types are not excluded. Examples are sound, which in its basic form after all is often used for alarm clocks, or possibly even tactile or olfactory stimuli, such as coffee or some obnoxious smell. For all other embodiments described and shown, it should be kept in mind that light is preferred, but is not exclusive of alternatives mentioned here. Correspondingly, stimulus sources and stimulus sensors are preferably, but not exclusively, light sources and light sensors, respectively.

In embodiments, the stimulus sensor comprises a sensor built into the control unit and/or an external sensor, the external sensor preferably being operably coupled to the control unit by a wire or a wireless network connection. It is for example possible to position the control system at or near the pillow or other place for the head of the sleeper. The stimulus level thus measured corresponds to the stimulus level experienced by the sleeper. This further increases the reliability of the system. In certain cases, it could be advantageous to use an external sensor, such as when the control system is rather heavy, or fixedly attached to a wall etc. Such an external sensor could be positioned on or near the same position. The sensor is for example connected to the control unit by a wire or cable, or by a network connection, such as Bluetooth®.

The stimulus sensor could be of any type that is suitable for outputting a measured value. A preferred stimulus sensor comprises a light sensor, such as photodiodes and phototransistors for a light sensor. If desired, some responsivity characteristic may be added, for example if a weighting is added for a different effectiveness in waking up a person, but a flat characteristic could also suffice. It is also possible to add a diffuser, an integrating sphere or the like to take into account a directivity of the light.

A stimulus sensor could also be used for determining whether the stimulus source used is actually capable of achieving a sufficient stimulus output. For example, sometimes one must replace a malfunctioning light source by a new one. In this case, the new light source could be judged by comparing the sensed light level for the new light source with that of the original light source. Likewise, this may be done with a built-in sensor or with an external sensor coupled to the control unit.

In an embodiment, the system comprises at least two stimulus sensors. By including two or more sensors, one is able to determine an average stimulus level. In such a case, the system may become even more reliable, in that the sensors may be positioned at at least two positions on or near the sleeper's head, such as to the left and to the right, possibly additionally above the head. One, or in particular the control unit, may thus take into account the fact that many people tend to turn their heads during sleep, which may change the position of the eyes with respect to the stimulus source used.

In particular, the control unit comprises a comparator for comparing a sensor signal value to a predetermined threshold value. Such a comparator is a useful device for processing the measured stimulus level. For example, the comparator may emit a signal if the measured stimulus level exceeds the threshold value, which indicates a useful wake up stimulus system, such as a useful stimulus source, position etc. The control unit may further comprise some kind of display, such as a light, an audible sound signal means, a display screen etc., to indicate a useful stimulus source etc.

The threshold value could be user-settable. This allows to adapt the system to a user's sensitivity. For example, a light sleeper may want to set a lower value than a heavy sleeper. Preferably, in the case of light being the stimulus, the threshold value corresponds to a (perceived) light level of at least 250 lux. It turns out that such a light level is an appropriate light level to be reached when waking people gradually, and with resulting wellness. It is of course not excluded to have an even higher threshold value, such as corresponding to about 400 lux. However, this is not often necessary, and could also lead to problems such as if the light sources become too bright themselves (i.e. a too high luminosity or candela level), which could lead to eye damage. Similar considerations apply for other types of stimuli, such as sound pressure levels In an advantageous embodiment, the system, and in particular the control unit, is arranged such that a stimulus output level, preferably a light level, increases according to a predetermined function. For example, the light output level increases in proportion to said function, which may be pre-programmed. Preferably, the predetermined function is an e-curve, as it was established that such a curve causes an appropriate release of melatonin, which promotes a satisfactory and relaxed waking up.

In a special embodiment, the length of the time period is between 10 and 60 minutes. Within such boundaries, waking up is experienced by most people as relaxed. In an advantageous embodiment, the length of the time period is user-determinable. This is e.g. advantageous if the time for sleeping is shorter than desired, yet a relaxing wake up procedure is desired. Then, a short time period such as 10 minutes could be selected. On the other hand, on a day off, the user could select a long time period, such as 60 minutes, to achieve a very strong wellness feeling.

In a particularly advantageous embodiment, the control unit is arranged to control the at least one stimulus source in dependence on a wake up stimulus level measured by the at least one stimulus sensor. By thus controlling the stimulus source(s) with the help of the sensor(s), a number of advantages is achievable.

First of all, ageing of the stimulus source, or some other cause of lowering of the intrinsic stimulus output level of the stimulus source(s) may be corrected. In such a case, when a lower output level is measured, the control unit may control the stimulus source(s) such that they receive more power, and provide a higher stimulus output level, now being sufficient, e.g. for following a desired time-dependent curve.

It is also possible to take into account a varying ambient stimulus level. For example, ambient lighting may vary according to the type of blinds, curtains etc., and to whether they are closed, fully closed etc. Furthermore, the time of year may have its influence on the stimulus level through various amounts of seasonal lighting, birds' chatter, and so on. Furthermore, the weather may have an important influence on the light level, as a clear sky is much brighter than a cloudy or rainy sky. Other factors could include headlights of passing cars, street lamps, advertising lights, and so on. Thus, if the ambient stimulus level is higher, the control unit of the system according to the invention could set a lower power level, to cause less additional stimulus and achieve a desired overall stimulus level, and vice versa. Especially in the case of varying light levels, such as a semi-cloudy sky during dawn, headlights or flickering advertising lights, the control unit can take away, or at least diminish, negative effects of the light level variation. An important effect of such control of total stimulus level to a desired level is that people do not awake prematurely, because the total stimulus level exceeds a person's wake up threshold, or vice versa remains below a threshold. This makes the system more reliable. A further advantage is that energy is saved, since use is made of ambient stimulus when possible.

In an embodiment, the system has a built-in clock and a wake up parameter input device. This allows a compact and reliable design. The clock may be any type, such as a quartz clock. The wake up parameter input device may be a dial, a keyboard, and so on. The system may then determine appropriate control signals based on its own clock, and to the desired wake up parameter, such as wake up time, starting time etc. In addition, the system could be arranged to receive a desired time period for waking up, etc.

However, it is also possible for the system to comprise an external clock and/or an external wake up parameter input device, or generally an input device for inputting at least the desired wake up parameter, the control unit being arranged to receive said input. A favorable embodiment comprises a control unit that is arranged to receive a desired wake up parameter from a cell phone, an electronic alarm clock, an mp3 player such as the Apple iPod®, or any other electronic device with a clock and a settable alarm. In particular, if a docking station or other interface is available, this can greatly simplify the communication with and control of such devices. Preferably, the system comprises such electronic device with a clock and a settable alarm. If necessary, the electronic device is arranged for outputting its alarm time to the control unit. This could be done via any desired protocol or other means of communication. For example, if an alarm clock normally shows the time, but on pressing an alarm time button shows the set alarm time, the signal responsible for showing the set alarm time could be used for sending to the control unit. An advantage of such a system according to the invention is that it may be made simpler. The electronic devices with a clock and settable alarm in principle have all the necessary features for setting the system of the invention, and the control unit may remain free from such input devices etc. A particularly well-suited example is a cell phone, with a clock, an alarm, input devices such as a fully equipped keyboard, and general communication functions. Furthermore, virtually everybody has at least one cell phone, and an extended use thereof is easily implemented.

In the system of the invention, the coupling could comprise at least one output terminal for the at least one stimulus source, and/or a transmitter arranged to emit a control signal to the at least one stimulus source and/or the at least one output terminal. Such an output terminal could be used to couple the stimulus source(s). Preferably, the output terminal comprises a socket for a plug or a lamp socket. A lamp socket suffices for releasably receiving a light source, such as an incandescent lamp. It is also possible to provide a plug for plugging in an external stimulus source, such as a standard wall plug. In this way, one is almost completely free in using external stimulus sources, such as those that were already available to the user, for example bed lamps.

Preferably, the stimulus source(s) and/or the output terminal(s) then comprise a receiver for receiving an emitted control signal and/or a stimulus source control unit for controlling a power supply to the stimulus source. This means that the stimulus sources and/or the output terminals could each comprise a receiver and/or a stimulus source control unit. For example, the receiver could be a radio receiver or antenna for receiving radio signals or signals for some network or the like, an infra red receiver, a receiver responsive to a PLC pulse and so on. In each case, the receiver could be adapted to the type of communication used. Similarly, power control may be arranged in a stimulus source control unit that could be responsive to a signal from the receiver. For example, a control signal emitted by a control unit of the system proper (i.e. not the control unit of an output terminal or stimulus source) could be a simple start signal for the stimulus source control unit, which could be, or comprise, a built-in unit that controls the stimulus output through a variable resistor or network, a pulse width modulation (PWM) signal or the like. Various such control mechanisms may be selected by the skilled person depending on the type of stimulus source used, and other criteria. In appropriate cases, a stimulus (light) source could be adapted to include suitable electronics in the (lamp) base or the like. An advantage of such output terminals is that in theory any stimulus source with the required (lamp) base could be used. Also, a light source with built-in control unit, and possibly a receiver, could be used to fit existing lamp sockets. Such lamps could advantageously be used in existing and possibly fixed lamp fixtures, such as ceiling lamps, bed lamps etc. A further advantageous embodiment in this respect will be given below.

In embodiments, the coupling comprises a conductive cable. For example in the case of output terminals or stimulus sources physically coupled to the control unit this cable may now allow additional types of control such as the reliable power-line communication (PLC) logic, which does not require transmitters or the like.

In certain embodiments, the system of the invention comprises at least one stimulus source coupled to the control unit. With such a "built-in" stimulus source, a good control over the functionality by the manufacturer is obtained. The stimulus source could be replaceable. Preferably, the system comprises at least two stimulus sources. This not only allows a higher stimulus level to be reached with similar sources such as lamps, or a similar level with lower power sources. It also allows much more intricate stimulus (such as lighting) patterns. The simplest case and the most obvious advantage is that it is now possible to provide stimulus on both sides of the pillow or the like. The disadvantage of a single stimulus source being screened by a person's head is decreased this way. This ensures that the experienced stimulus level is controlled better to the desired level. Providing more stimulus sources can make the system even more reliable. Note that the system may thus also comprise at least two output terminals, wires etc., to accommodate the stimulus sources.

Another advantage of providing more than one stimulus source is the possibility of waking up a particular person in a group of more than one person with a single system. Two or more people could enter their desired wake up parameter, and the control unit controls appropriate stimulus sources, such as those nearest the relevant person, in order to allow a person to wake up with the desired parameter without waking up other persons.

Another advantageous embodiment involving a plurality of stimulus sources is arranged to provide a desired stimulus program. For a lighting example, in a dusk-like setting, the general lighting could diminish to simulate dusk, while a separate light source provides a reading function, if desired. Similarly, dawn may be simulated by a general lighting of the room, while dedicated light sources are used for specifically waking up one or more persons. Other settings will easily come to the minds of the skilled persons.

Up to now the invention has been described in relation to waking up with a general stimulus. As mentioned, light is preferred due to its versatility and controllability. However, the same principles could be used for waking up by means of sound etc. Hence, in addition to or in replacement of any instance of "stimulus" or in particular "light" in this application, one could also read "sound", etc. Hence, the invention also provides a wake up system, arranged to control a sound source, and comprises a sound sensor. Similarly, advantageous embodiments follow the lines of those of the light-based wake up lighting control system of the invention. E.g. the system could comprise one or more sound sources, such as radios, mp3 players and so on. Note however, that the "light" version is preferred, because light sources are controlled more easily, and are believed to have a more relaxing and more pleasant effect.

In addition, it is possible for the system according to the present invention to further include any other device controllable by or via the control unit. This could comprise e.g. baby monitoring gear, a coffee machine, which could even further relax waking up by providing pleasing smells and/or sounds, and so on.

In embodiments, the at least one stimulus source comprises any suitably controllable light source, such as incandescent lamps, halogen incandescent lamps, an LED or LED assembly and so on. Here, controlling the light output could be achieved by simply varying the voltage level to a desired level. In general, a controllable light source is intended to comprise a fixed light source with a controllable attenuator. In this way, for example gas discharge lamps could also be used, which are normally only controllable with a flash start that could be too bright too suddenly, and thus less well-suited for use in the present system. By using a controllable attenuator, such as moveable blinds, screens, Kerr effect filters etc., use may be made of fixed or substantially less well-controllable light sources, such as fluorescent lamps, which allows using their particular advantages such as high efficiency lighting without too bright lighting surfaces.

Another embodiment that allows the use of less well, or per se insufficiently controllable stimulus sources comprises a combination of a controllable stimulus source and an insufficiently controllable stimulus source. For example, the control unit may be set to first start the controllable stimulus source(s) to increase a stimulus level to just above the starting level of the insufficiently controllable stimulus source(s), such as the flash start level of fluorescent lamps. By dimming (turning down, in general) the controllable stimulus source at substantially the same time when the insufficiently controllable stimulus source starts emitting, the total stimulus level could be sufficiently well-controlled. After the start of the insufficiently controllable stimulus source, the control unit could then further power up the latter to increase the stimulus level. Especially if the stimulus sensor and the controllable stimulus source have a sufficiently short response time, such as for a suitable photodiode and LEDs, respectively, the total stimulus level is controllable without any unwanted variations that could wake up a person, e.g. by being perceivable through closed eyelids.

In embodiments, that have already been subtly indicated above, the control unit is partly housed in the at least one output terminal and/or stimulus source. Systems with such distributed control may be more flexible in that parts are more easily interchangeable, or can be added more easily, such as more lamps. Hence, the system may comprise such special output terminal and/or stimulus source, with a part of the control means.

The invention also relates to a socket with a power connection and arranged to releasably receive a controllable stimulus source arranged to provide a wake up stimulus, the socket further comprising a control unit that is arranged to receive an external control signal and to control the stimulus source in dependence on said external control signal, in such a way that the stimulus source provides a gradually increasing stimulus output, in dependence on said external control signal, in particular for use in a system according to the invention, and in particular comprising a control unit of a system according to the invention. In embodiments, the stimulus source is arranged to provide the wake up stimulus in dependence on the control signal at least during a time period before an input desired wake up time.

The invention also relates to a stimulus source that is releasably receivable in a socket and is arranged to provide a wake up stimulus, further comprising a control unit that is arranged to receive an external control signal and to control the stimulus source in dependence on said signal, in such a way that the stimulus source provides a gradually increasing stimulus output, in dependence on said external control signal, in particular for use in a system according to the invention, and in particular comprising a control unit of a system according to the present invention. In embodiments, the control signal comprises, or comprises information about, a wake up parameter, and preferably, the stimulus source is arranged to provide the wake up stimulus in dependence on the control signal at least during a time period before the input wake up time.

Since the above sockets and stimulus sources, preferably lamp sockets and light sources, are in principle parts of certain embodiments of a wake up stimulus control system according to the present invention, its advantages will be clear without further elucidation. Details, as well as special embodiments corresponding to those of special systems according to the invention, can similarly be derived from the description above.

The invention also relates to a stimulus control device comprising a control unit arranged to receive a wake up parameter input from an external parameter input device, and to control at least one stimulus source that is controllable by the control unit, and a coupling for operably coupling at least one stimulus source to the control unit, in such a way that the stimulus source provides a gradually increasing stimulus output, in dependence on said input wake up parameter. In particular, the wake up parameter comprises a desired wake up time, and the stimulus source is arranged to provide the gradually increasing stimulus output at least during a time period before the input wake up time. In particular, the stimulus comprises light. In embodiments, the stimulus control device is arranged for use in a system according to the present invention. Such a stimulus control device is a very simple form of control device. It could take its time information from an external device, such as a cell phone, as described above. It could be used to control a stimulus source that is (to be) connected thereto. Such a stimulus control device is very well suited for various uses. It can also profit from the various features of all embodiments of the system according to the invention, described above.

BRIEF DESCRIPTION OF THE DRAWINGS

These and other aspects of the invention are apparent from and will be elucidated with reference to the embodiments described hereinafter.

In the drawings.

DETAILED DESCRIPTION OF THE PREFERRED EMBODIMENTS

Figure 2:
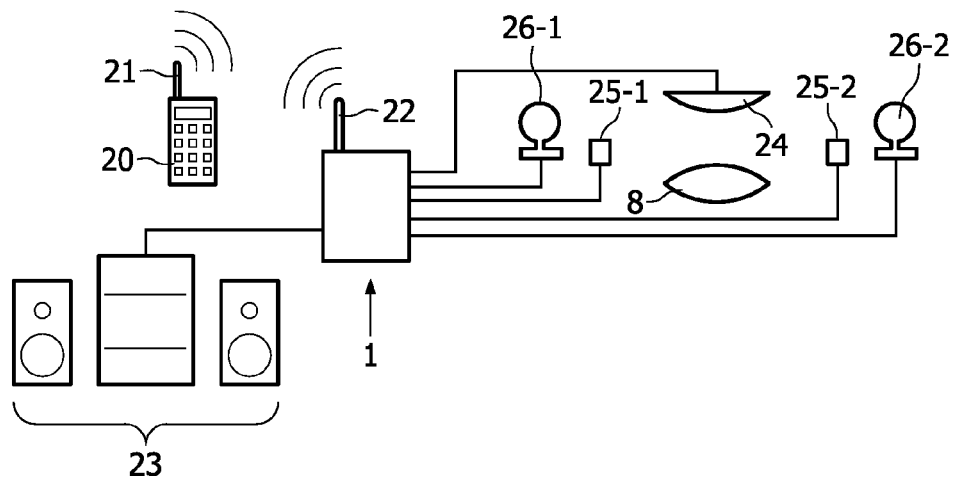
FIG. 2 diagrammaticaly shows another embodiment of a wake up stimulus control system according to the invention.

A remark made here is that, for simplicity, all embodiments shown relate to waking up with light, in other words with light as a stimulus. It is to be understood that the invention is not limited to such type of stimulus, and sound or other sensory stimuli could also be used. An explicit example that also uses sound is shown in FIG. 2.

Figure 1:
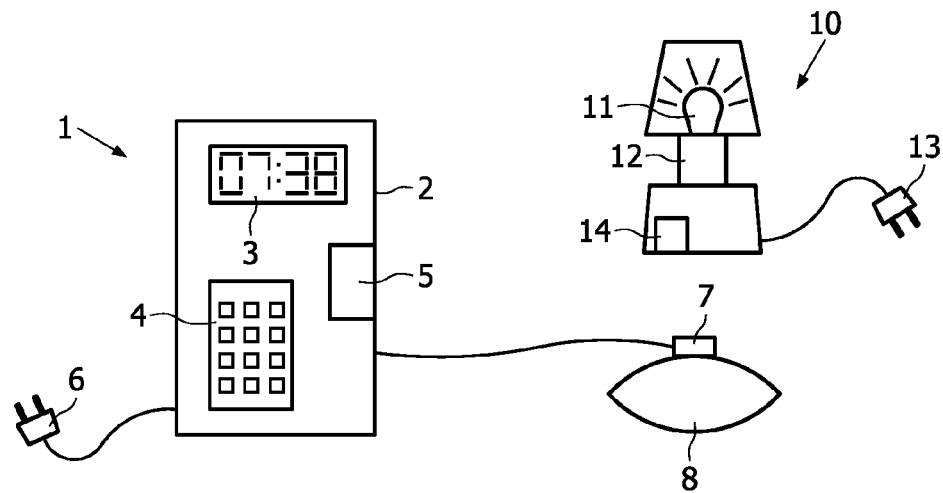
FIG. 1 very diagrammatically shows an embodiment of a wake up stimulus control system according to the invention.

FIG. 1 very diagrammatically shows an embodiment of a wake up stimulus control system according to the invention. Herein, 1 generally denotes a stimulus control device, and comprises a housing 2, a display 3, a keyboard 4, a transmitter (or transceiver) 5, and a wall plug 6.

The lighting control device 1 is connected to a light sensor 7, and is a wake up lighting control system according to the invention. A pillow is denoted by 8.

A lamp is denoted by 10, and comprises a light source 11, a lamp socket 12, a wall plug 13 and a receiver (or transceiver) 14.

The lighting control device could be an alarm clock that is arranged to communicate with a lamp 10, or more precisely a light source 11. In FIG. 1, such communication, e.g. RF communication, is achieved through a transmitter (5) receiver (14) combination, or alternatively a transmitter transmitter combination. Infrared communication is also possible. The control device 1 comprises suitable circuitry for providing a control signal that controls the lamp 10 to emit a gradually decreasing (or decreasing) amount of light. The circuitry could comprise any microprocessor, printed circuit board and so on. It suffices for most light sources 11, such as incandescent or halogen bulbs, to receive an increasing supply voltage. Alternatively, a pulse width modulated power signal and so on could also suffice.

Not shown is a power controller in the lamp 10, which translates the control signal into a power signal for the light source. Any known power controller may be used for this purpose, such as a variable resistor, a PWM power controller and so on.

In use, the user can enter a desired wake up time, e.g. through keying it in on keyboard 4, and checking the result, the actual time etc. on display 3. If desired and arranged for, the user could also enter a desired time period during which the light level is to be increased (or decreased).

The wall plug 6 is shown not only as a power connector, but could also serve as a pathway for communication with the lamp 10, via PLC logic, through corresponding wall plug 13, provided both the control device 1 and the lamp are connected to the same power line.

The light sensor 7 is shown connected via a wire, but could also be connected via a network, transceiver etc. The sensor measures the light level of lamp 10 at the position of the pillow 8, i.e. at the position of the sleeper. Variations in the received and perceived light level, due to ambient light, ageing of the light source 11 and so on may be accounted for by a measured light level.

The control device 1 may comprise a comparator (not shown separately) for comparing the measured light level to a desired level, or a threshold. In an example, the threshold is about 250 lux. If the light sensor measures such a value, the lighting is deemed sufficient for efficiently and relaxedly waking up most people. Then, the display could show some "o.k."-sign, such as a green light, or the word "o.k.".

FIG. 2 diagrammatically shows another embodiment of a wake up stimulus control system according to the invention. Herein, as in all of the drawings, similar parts are denoted by the same or closely related reference numerals.

In FIG. 2, 20 denotes a cell phone, with a transmitter antenna 21. A receiver antenna 22 is provided on the control device 1, while 23 denotes audio equipment.

A ceiling lamp is denoted by 24, a first and a second sensor by 25-1 and 25-2, respectively, and a first and a second bedlamp by 26-1 and 26-2, respectively.

In this embodiment, there are two sensors, 25-1 and 25-2, positioned around the pillow 8. This allows more accuracy in the actually perceived light level. The control device 1 may use both measurements, e.g. to determine an average light level value. The light level may be due to any combination of lit lamps, such as the ceiling lamp 24 or bedlamps 26-1 and 26-2. Furthermore, there may be ambient light from dawn or dusk, external lamps or lights et cetera, none of which are shown in FIG. 2. Nevertheless, this light will also be measured by the sensors 25-1 and 25-2, and the measured values will be supplied to the control device 1. Said device can calculate how to control the various light sources in order to achieve a gradually increasing light level such that a sleeper is awoken at a desired time, assuming the sleeper awakes at a certain light level.

The desired wake up time could be entered by setting an alarm time in the cell phone 20. This cell phone is arranged for the set alarm time to be read by the control device 1. Thereto, the cell phone 20 and the control device 1 can communicate, e.g. via a transmitter antenna 21 and a receiver antenna 22 respectively. The control device 1 can then determine an appropriate starting time to start controlling the lamps 24, 26 from the desired wake up time, to be a certain time period before the wake up time. This time period could be built-in and fixed, or could also be user-settable, such as on the control device 1 or also on the cell phone 20. It is noted that the described combination of transmitter and receiver antennae suffices. However, in practice it provides a more flexible system if both are transceiver systems, in order to allow a two-way communication.

The control device is shown also to control audio equipment 23. This could e.g. serve a final wake up signal at the desired wake up time, or could be a similarly regulated audio sound level.

Another possibility in the embodiment shown is to regulate the wake up procedure for two different people, i.e. two different pillows 8. In such a case, there would be two pillows 8, and the sensors 25-1 and 25-2 would provide a separate reading for the two pillows, one for each person. The control unit could then select a single lamp 26-1 or 26-2 corresponding to the person desiring to be awoken at the particular time. Other numbers, such as more than two people, more than two sensors, more than one sensor per person, more than two light sources in total or more than one light source per person are of course also possible. The control system could then control a desired subset of the light sources and/or sensors. In a particular embodiment, such a plurality of sensors and/or sources could be used to control the latter to provide a more even stimulus level. For example, if four light sources are provided on the four corners of a sleeping room, and two sensors, one on each side of the pillow, then the control unit may take ambient light into account, and provide more even lighting of the total room by adapting the light sources according to the sensor reading. Such more even lighting prevents a sudden increase in perceived light level if the user e.g. turns around on his pillow.

In addition, or alternatively, some general dawn or dusk simulation could be performed with the ceiling lamp 24. Alternatively, 26-1 and/or 26-2 could serve as reading lamps, while the general light level of ceiling lamp 24 is decreased, also simulating dusk, for relaxed falling asleep.

Figure 3:
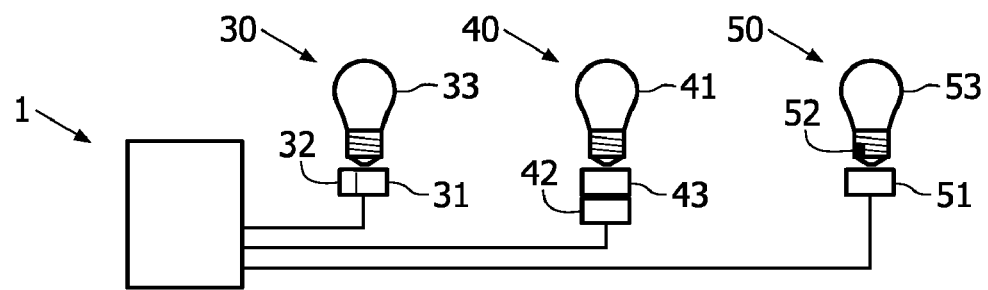
FIG. 3 diagrammatically shows another embodiment of the system, with different light sources and/or lamp sockets.

FIG. 3 diagrammatically shows another embodiment of the system, with different light sources and/or lamp sockets.

Herein, the control device 1 is connected to three lamps 30, 40 and 50. The first lamp 30 comprises a special lamp socket 31 with a light source control unit 32, and an ordinary light bulb 33.

The lamp socket 31 is designed to receive the light bulb 33, and thereto has e.g. a suitable thread or the like. The lamp socket 31 also comprises a light source control unit 32 that is arranged to receive an external control signal and furthermore to control power supply to the light bulb 33. Shown here is a wire connection between the lamp socket 31 and the control device 1, but it could also be a wireless connection. The connection shown is e.g. a Power-Line Communication, in which at least one signal is sent to and received by the light source control unit 32. The signal could simply be a start signal, to start a fixed program of increasing (or decreasing) power to the light source. It could also include information on the desired time period for increasing. The signal could also be a recurrent and/or continuous signal, e.g. to take into account sensor input to the central control device 1.

Upon receipt of the signal, the light source control unit 32 will start supplying power to the light bulb 33, in order to obtain an increasing light level. A special increase function may be built into the light source control unit 32, such as an exponential curve, up to a maximum light level.

The second lamp 40 also comprises a conventional light bulb 41, and a conventional lamp socket 42 (shown very much simplified here), and additionally an adapter unit 43. The adapter unit 43 is receivable in the lamp socket 42, and in turn is arranged to receive a light bulb 41, or if desired some other type of light source. The adapter unit 43 comprises a light source control unit similar to the one designated 32 in lamp 30, and hence can also receive an external control signal from control device 1, and control light source 41. An advantage of this embodiment is that any conventional lamp may be rearranged to become part of the system according to the invention, simply by adding the adapter 43 between the normal lamp socket 42 and the light bulb 41.

An alternative to this embodiment is an adapter plug that may be inserted into a wall socket. The plug of the device (light source) may then be inserted into a socket of the adapter plug. The same functionality as mentioned above for the lamp socket could also be built into the adapter plug.

The third lamp 50 comprises a conventional lamp socket 51 and a special light bulb 53 with a built-in light source control unit 52, which has the same functionality of the light source control units in the first and second lamps 30 and 40, and will not be discussed again here. By building the light source control unit 52 into the light bulb 53, the number of steps when replacing a conventional light bulb for the special one shown here is diminished. Furthermore, since the actual light source and the light source control unit are integrated, the control processes may be optimized for said light source. E.g. the maximum light level and the ageing are known beforehand, and these may be taken into account when the power to the light source is increased.

Figure 4:
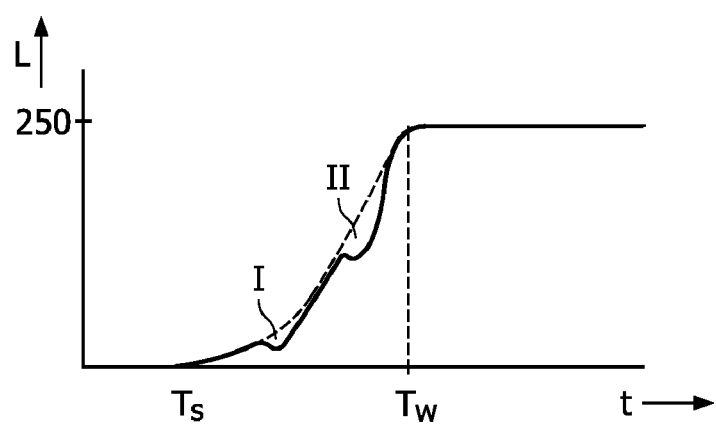
FIG. 4 shows an example of stimulus control for waking up by the system of the invention.

FIG. 4 shows an example of light control for waking up by the system of the invention.

The graph shows a dashed line that represents the total light level in lux, as desired for relaxed waking up. The solid line represents the light level as produced by the light source(s) in the room controlled by the system.

First of all, the dashed curve represents substantially an exponential function, starting at the starting time Ts, and running until the desired wake up time Tw. The time period between Ts and Tw is for example 30 minutes, and may be settable. After Tw, the light level is shown to be constant, but it could also continue increasing beyond the level of 250 lx.

The solid line represents the lighting by light source(s) controlled by the system of the invention. When no external light manages to reach the room, the solid line would copy the dashed line. However, in this case, let's assume there is light from dawn, with a cloudy sky, in two cases the sun succeeding to peep through the clouds. These occasions are indicated by I and II. Because at I and II the sun adds light, the overall light level could become either too high, causing premature waking up of the sleeper, or at least show too quick an increase, the system being designed to correct for this sunlight. It does this by measuring the total light level with a sensor (not shown), and adapts the power control of the controlled light source(s), such that the total light level resembles the desired (dashed) curve as closely as possible.

It is repeated here that an important aspect of the invention is that the wake up stimulus control system comprises a sensor that allows corrections of the stimulus level.

Another aspect is the provision of a control device that allows externally inputting a desired wake up parameter and that is arranged to control a stimulus source, that can be coupled to the control device to increase a stimulus level in dependence on said wake up parameter, such as before a wake up time. The embodiments shown are not intended to be limiting, but are merely given as examples to illustrate the invention.

The invention claimed is:

1. A wake up stimulus control system, comprising
a control unit arranged to receive a user-determinable wake up parameter input and to control at least one stimulus source for supplying a wake up stimulus; and
a coupling for operably coupling said at least one stimulus source to said control unit, wherein the at least one stimulus source is controllable by the control unit in such a way that the stimulus source provides a gradually increasing stimulus output, in dependence on said input wake up parameter,
wherein the system further comprises at least one stimulus sensor arranged for sensing an ambient stimulus level proximate a user of the wake up stimulus control system, said ambient stimulus level being influenced at least in part by the stimulus output of said at least one stimulus source, said stimulus sensor being operably coupled to the control unit;
and wherein the control unit controls the at least one stimulus source in dependence on the ambient stimulus level sensed by the at least one stimulus sensor.

2. The wake up stimulus control system as claimed in claim 1, wherein said wake up parameter comprises a desired wake up time, and wherein the at least one stimulus source provides said gradually increasing stimulus output at least during a time period before the desired wake up time.

3. The wake up stimulus control system as claimed in claim 1, wherein the wake up stimulus comprises light.

4. The wake up stimulus control system as claimed in claim 1, wherein the stimulus sensor comprises a sensor built into the control unit and/or an external sensor, the external sensor preferably being operably coupled to the control unit by a wired or a wireless network connection.

5. The wake up stimulus control system as claimed in claim 1, wherein the control unit comprises a comparator for comparing a sensor signal value to a predetermined threshold value.

6. The wake up stimulus control system as claimed in claim 1, arranged such that a stimulus output level increases according to a predetermined function.

7. The wake up stimulus control system as claimed in claim 1, wherein the coupling comprises at least one output terminal for the at least one stimulus source, and/or a transmitter arranged to emit a control signal to the at least one stimulus source and/or the at least one output terminal.

8. The wake up stimulus control system as claimed in claim 1, wherein said wake up stimulus control system comprises at least one stimulus source coupled to the control unit.

9. The wake up stimulus control system as claimed in claim 7, wherein the control unit is partly housed in the at least one output terminal and/or stimulus source.

10. The wake up stimulus control system as claimed in claim 3, wherein the control unit comprises a comparator for comparing a sensor signal value to a predetermined threshold value corresponding to a light level of at least 250 lx.

11. The wake up stimulus control system as claimed in claim 1, arranged such that a stimulus output level, comprising a light level, increases according to a predetermined function corresponding to an e-curve.

12. The wake up stimulus control system as claimed in claim 1, wherein said wake up stimulus control system comprises at least two stimulus sources coupled to the control unit.

13. A socket with a power connection and being arranged to releasably receive a controllable stimulus source arranged to provide a wake up stimulus, the socket further comprising a control unit that is arranged to receive an external control signal and to control the stimulus source in dependence on said control signal, in such a way that the stimulus source provides a gradually increasing stimulus output, in dependence on said external control signal, wherein the control unit is arranged to control the at least one stimulus source in dependence on an ambient stimulus level measured by an external stimulus sensor positioned proximate to a user, said ambient stimulus level being influenced at least in part by the stimulus output of said at least one stimulus source, and said external stimulus sensor being operably coupled to the control unit.

14. A stimulus source that is releasably receivable in a socket and is arranged to supply a wake up stimulus, the stimulus source further comprising a control unit that is arranged to receive an external control signal and to control the stimulus source in dependence on said signal in such a way that the stimulus source provides a gradually increasing stimulus output in dependence on said external control signal, wherein the control unit is arranged to control the stimulus source in dependence on an ambient stimulus level measured by an external stimulus sensor positioned proximate to a user, said ambient stimulus level being influenced at least in part by the stimulus output of said stimulus source, and said external stimulus sensor being operably coupled to the control unit.

15. A stimulus control device comprising a control unit arranged to receive a wake up parameter input from an external parameter input device, and to control at least one stimulus source that is controllable by the control unit and is arranged to provide a wake up stimulus; and a coupling for operably coupling the at least one stimulus source to said control unit in such a way that the stimulus source provides a gradually increasing stimulus output in dependence on said wake up parameter input wherein the control unit is arranged to control the at least one stimulus source in dependence on an ambient stimulus level measured by an external stimulus sensor positioned proximate to a user, said ambient stimulus level being influenced at least in part by the stimulus output of said at least one stimulus source, and said external stimulus sensor being operably coupled to the control unit.

16. The stimulus control device as claimed in claim 15, wherein the stimulus comprises light and/or wherein the wake up parameter comprises a desired wake up time.

* * * * *